(12) United States Patent
Polito et al.

(10) Patent No.: US 10,010,508 B1
(45) Date of Patent: Jul. 3, 2018

(54) MTAB-TA-COATED GOLD NANORODS AND METHOD OF FABRICATION

(71) Applicant: The United States of America, as represented by the Secretary of the Air Force, Washington, DC (US)

(72) Inventors: Anthony B Polito, Springboro, OH (US); Saber M Hussain, Beavercreek, OH (US)

(73) Assignee: The United States of America as represented by the Secretary of the Air Force, Washington, DC (US)

(*) Notice: Subject to any disclaimer, the term of this patent is extended or adjusted under 35 U.S.C. 154(b) by 0 days.

(21) Appl. No.: 15/379,581

(22) Filed: Dec. 15, 2016

(51) Int. Cl.
*A61K 9/28* (2006.01)
*A61K 9/20* (2006.01)
*A61K 33/24* (2006.01)

(52) U.S. Cl.
CPC .......... *A61K 9/2826* (2013.01); *A61K 9/2013* (2013.01); *A61K 33/24* (2013.01)

(58) Field of Classification Search
CPC ..... A61K 9/2826; A61K 9/2013; A61K 33/24
See application file for complete search history.

(56) References Cited

PUBLICATIONS

Polito et al. (Surface chemistry manupilation of gold nanorods preserves optical properties for bio-imaging applications, J. Nanopart. Res., 2015, Abstract, published Jan. 12, 2015 (Year: 2015).*

Polito III (Manipulation of gold nanorod physicochemical properties to enhance biocompatibility, uptake and intracellular preservation of optical properties for bio-imaging and plasmonic photo therapeutic applications, PhD Thesis, 2015, Aug. 10, 2015 (Year: 2015).*

Ejima, Hirotaka, et al. One-Step Assembly of Coordination Complexes for Versatile Film and Particle Engineering, http://science.sciencemag.org, 2013.

(Continued)

*Primary Examiner* — Trevor M Love
(74) *Attorney, Agent, or Firm* — AFMCLO/JAZ; Timothy Barlow (57) ABSTRACT

11-mercaptoundecyl trimethylammonium bromide gold nanorod (MTAB-GNR) coated with tannic acid (TA), useful for biological cellular imaging. A method of synthesizing tannic acid-coated 11-mercaptoundecyl trimethylammonium bromide gold nanorods (MTAB-TA GNRs) comprising presenting 11-mercaptoundecyl trimethylammonium bromide gold nanorods (MTAB-GNRs) in solution; functionalizing the MTAB-GNRs with tannic acid (TA) added to the MTAB-GNRs, the tannic acid configured to form a coating around the MTAB-GNRs forming MTAB-TA GNRs. The functionalizing step may further comprise adding a sodium chloride solution to the MTAB-TA GNR solution, and/or adding a MOPS buffer to the solution of tannic acid with MTAB-GNRs, and the tannic acid MTAB-GNR solution may be vortexed after each step. The MTAB-TA GNR solution may be centrifuged to separate the MTAB-TA GNRs from residual tannic acid and supernatant, and sterile water may be added to the MTAB-TA GNR solution and centrifuging performed to remove residual tannic acid from the MTAB-TA GNRs.

12 Claims, 7 Drawing Sheets

(56) References Cited

PUBLICATIONS

Ejima, Hirotaka, et al. Supplemental Materials for One-Step Assembly of Coordination Complexes for Versatile Film and Particle Engineering, http://science.sciencemag.org, 2013.

DeBrosse, Madeleine, et al. High Aspect Ratio Gold Nanorods displayed augmented cellular internalization and surface chemistry mediated cytotoxicity, Mater. Sci. Eng., 2013.

Untener, E., et al. Tannic Acid Coated Gold Nanorods Demonstrate a Distinctive Form of Endosomal Uptake and Unique Distribution within Cells, ACS Appl. Mater. Interfaces 2013.

Alkilany, A. et al. Toxicity and cellular uptake of gold nanoparticles: what we have learned so far? J. Nanopart Res. 2010.

Park, K. et al. Synthesis of Complex Au/Ag Nanorods by Controlled Overgrowth, Adv. Mater. 2008.

Vigderman, L. et al. Quantitative Replacement of Cetyl Trimethylammonium Bromide by Cationic Thiol Ligands on the Surface of Gold Nanorods, Angew. Chem. Int. Ed. 2012.

\* cited by examiner

Summary of the differential intracellular distribution pattern of TA-coated and uncoated MTAB GNRs. After internalization by human lung cancer cells (A549), uncoated MTAB GNRs displayed high intracellular aggregation. This resulted in a degradation of optical properties. On the contrary, TA-coated MTAB GNRs displayed low intracellular aggregation and preserved NIR optical properties.

MTAB-TA-COATED GOLD NANORODS AND METHOD OF FABRICATION

RIGHTS OF THE GOVERNMENT

The invention described herein may be manufactured and used by or for the Government of the United States for all governmental purposes without the payment of any royalty.

FIELD OF THE INVENTION

The present invention relates generally to coated gold nanorods and, more particularly, to MTAB-TA-coated gold nanorods and methods of synthesizing them.

BACKGROUND OF THE INVENTION

Nanotechnology holds great potential, and nanomaterials are increasingly being developed for use in industrial, military, and consumer products including a vast array of biomedical applications. Gold nanorods (GNRs) are of particular interest due to their unique optical region absorbance, emission, and electronic properties. Based on these unique characteristics, GNRs have been used in a vast array of biomedical applications. However, the combination of responses from GNRs including elicited toxicity, poor cellular uptake, and loss of NIR optical properties due to intracellular aggregation remain obstacles for nanobased biomedical applications. The toxicity of GNRs is known largely to be due to free and surface-associated cetyl trimethylammonium bromide (CTAB), a cationic surfactant used in the aqueous synthesis of GNRs. Two main strategies have been reported to overcome this surfactant's cytotoxicity: replacement by post-synthesis ligand exchange or noncovalent overcoating by chemical cover layering through electrostatic attraction. Unfortunately, some commonly used surface modifications, for example, polyethylene glycol (PEG) functionalization, can significantly lower cellular uptake of the GNRs into cells, reducing their use in biomedical applications. Furthermore, overcoatings can break down in biological environments over time, resulting in surface leaching of the CTAB, so chemical stabilization by overcoating does not guarantee that the CTAB toxicity is completely mitigated.

Previous studies have reported that TA-coated (tannic acid) GNRs (MTAB-TA GNRs) show reduced toxicity, demonstrate a distinctive form of endosomnal uptake, and display a unique intracellular distribution pattern that reduces particle aggregation. Unfortunately, as the CTAB-TA GNR's aspect ratio (AR) increases, so does the toxicity, possibly due to the remaining CTAB.

To lower the toxicity of the GNRs, the removal or exchange of the CTAB from the GNRs may be performed, e.g. with MTAB. GNRs coated with MTAB (11-mercaptoundecyltrimethylammonium bromide) have been synthesized, but limited information is available in terms of their biocompatibility and characterization within biological matrices. However, it was found that 40% of the MTAB GNRs were taken up by the cells, compared to less than 1% of their PEGylated analogs, exceeding the previously-reported GNR uptake values. However, published TEM (transmission electron microscopy) images showed extensive aggregation of intracellular particles (GNRs), causing a loss of their near infrared (NIR) optical priorities. In particular, the intracellular features exhibited close proximity side-by-side assembly of GNRs, which can result in blue shift of plasmon resonance emissions moving the GNRs spectra out of the target NIR "water window" needed for biomedical applications.

Thus there remains a need for methods of synthesizing gold nanorods (GNRs) with enhanced biocompatibility and cellular uptake, while preventing particle aggregation to preserve key NIR optical properties.

SUMMARY OF THE INVENTION

The present invention overcomes the foregoing problems and other shortcomings, drawbacks, and challenges of gold nanorods (GNRs) with enhanced biocompatibility and cellular uptake, while preventing particle aggregation to preserve key NIR optical properties. While the invention will be described in connection with certain embodiments, it will be understood that the invention is not limited to these embodiments. To the contrary, this invention includes all alternatives, modifications, and equivalents as may be included within the spirit and scope of the present invention.

In a first embodiment of the invention, an 11-mercaptoundecyl trimethylammonium bromide gold nanorod (MTAB-GNR) is coated with tannic acid (TA). This structure provides several advantages, including enhanced biocompatibility and cellular uptake, while preventing particle aggregation and preserving key NIR optical properties.

According to a second embodiment of the invention, a method of synthesizing tannic acid-coated 11-mercaptoundecyl trimethylammonium bromide gold nanorods (MTAB-TA GNRs), comprises presenting one or more 11-mercaptoundecyl trimethylammonium bromide gold nanorods (MTAB-GNRs) in solution; and functionalizing the MTAB-GNRs with tannic acid (TA) added to the MTAB-GNRs in solution, wherein the tannic acid is configured to form a coating around the MTAB-GNRs and MTAB-TA GNRs are formed. TA may spontaneously form a coating, i.e. shell, layer, lattice, matrix, or capsule, around the GNRs. Accordingly, the solution includes MTAB-TA GNRs in addition to any excess TA or MTAB GNRs, if any. This process results in the formation of MTAB-TA GNRs having enhanced biocompatibility and cellular uptake, while preventing particle aggregation to preserve key NIR optical properties, as described above.

According to another embodiment of the invention, the functionalizing step may further comprise vortexing the tannic acid MTAB-GNR solution. Vortexing the solution may suspend and distribute the various components of the solution effectively, which may promote the formation of greater numbers of MTAB-TA GNRs. Vortexing may be performed after each step, as desired. To be clear, the MTAB-TA GNRs are not dissolved in the solution but are merely present in the solution in order to receive one or more components which may be in the solution or introduced in the solution, e.g. TA.

According to a further embodiment of the invention, the functionalizing step may further comprise adding a solution of sodium chloride to the solution of tannic acid with MTAB-GNRs. The sodium chloride helps to reduce the agglomeration of the TA when the buffer is added.

According to another embodiment of the invention, the functionalizing step may further comprise vortexing the tannic acid MTAB-GNR solution. Vortexing the solution may suspend and distribute the various components of the solution effectively, which may promote the formation of greater numbers of MTAB-TA GNRs.

According to a further embodiment of the invention, the functionalizing step may further comprise adding a MOPS buffer (3-(N-morpholino)propanesulfonic acid) to the solution of tannic acid with MTAB-GNRs. The MOPS Buffer raises the pH and helps to stabilize the TA coating around the MTAB-GNR.

According to another embodiment of the invention, the functionalizing step may further comprise vortexing the tannic acid MTAB-GNR solution. Vortexing the solution may suspend and distribute the various components of the solution effectively, which may promote the formation of greater numbers of MTAB-TA GNRs.

According to a further embodiment of the invention, the functionalizing step may further comprise centrifuging the MTAB-TA GNR solution to separate the MTAB-TA GNRs from residual tannic acid and supernatant.

According to another embodiment of the invention, the functionalizing step may further comprise adding sterile water to the MTAB-TA GNR solution and centrifuging to remove residual tannic acid from the MTAB-TA GNRs. This step may be performed several times, as desired, in order to remove excess tannic acid.

According to a further embodiment of the method of synthesizing tannic acid-coated 11-mercaptoundecyl trimethylammonium bromide gold nanorods (MTAB-TA GNRs), the functionalizing step may further comprise adding a solution of sodium chloride to the solution of tannic acid with MTAB-GNRs; adding a MOPS buffer (3-(N-morpholino) propanesulfonic acid) to the solution of tannic acid with MTAB-GNRs; and centrifuging the MTAB-TA GNR solution to separate the MTAB-TA GNRs from residual tannic acid and supernatant.

According to another embodiment of the invention, the functionalizing step may further comprise vortexing the tannic acid MTAB-GNR solution after each addition. Vortexing the solution may suspend and distribute the various components of the solution effectively, which may promote the formation of greater numbers of MTAB-TA GNRs.

According to a further embodiment of the invention, the functionalizing step may further comprise adding sterile water to the MTAB-TA GNR solution and centrifuging to remove residual tannic acid from the MTAB-TA GNRs. The addition of sterile water and centrifuging may be repeated as necessary in order to remove residual tannic acid. This process is advantageous in that it results in the synthesis of MTAB-TA GNRs which are free of residual TA and supernatant, rendering the MTAB-TA GNRs ready for cellular uptake and imaging.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

FIGS. 4A-4A2 depict representative TEM images and GNR uptake of MTAB GNRs by ICP-MS;

FIGS. 4B-4B1 depict representative TEM images and GNR uptake of MTAB-TA GNRs by ICP-MS;

FIGS. 5A-5A6 depict TEM images of the intracellular distribution pattern of MTAB GNRs;

FIGS. 5B-5B5 depict TEM images of the intracellular distribution pattern of MTAB-TA GNRs;

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

One or more 11-mercaptoundecyl trimethylammonium bromide gold nanorods (MTAB-GNR) may be coated with tannic acid (TA), according to the present invention, in order to make tannic acid MTAB gold nanorods (MTAB-TA GNRs). This structure provides several advantages, including enhanced biocompatibility and cellular uptake, while preventing particle aggregation to preserve key NIR optical properties.

According to a second embodiment of the invention, a method of synthesizing tannic acid-coated 11-mercaptoundecyl trimethylammonium bromide gold nanorods (MTAB-TA GNRs), comprises presenting one or more 11-mercaptoundecyl trimethylammonium bromide gold nanorods (MTAB-GNRs) in solution; and functionalizing the MTAB-GNRs with tannic acid (TA) added to the MTAB-GNRs in solution, wherein the tannic acid, e.g. 24 mM solution, is configured to form a coating around the MTAB-GNRs and MTAB-TA GNRs are formed. This process results in the formation of MTAB-TA GNRs having enhanced biocompatibility and cellular uptake, while preventing particle aggregation to preserve key NIR optical properties, as described above.

The functionalizing step may further comprise vortexing the tannic acid MTAB-GNR solution. Vortexing the solution may suspend the various components of the solution effectively, which may promote the formation of greater numbers of MTAB-TA GNRs. The functionalizing step may further comprise adding a solution of sodium chloride, e.g. 1.5 mM solution, to the solution of tannic acid with MTAB-GNRs. The sodium chloride helps to reduce the agglomeration of the TA when the buffer is added. Vortexing the solution may suspend the various components of the solution effectively, which may promote the formation of greater numbers of MTAB-TA GNRs, and vortexing may be performed after each step, if desired.

The functionalizing step may further comprise adding a MOPS buffer (3-(N-morpholino)propanesulfonic acid), e.g. 20 mM. pH 7.4, to the solution of tannic acid with MTAB-GNRs. The MOPS Buffer raises the pH and helps to stabilize the TA coating around the MTAB-GNR.

In addition, or in the alternative, the functionalizing step may further comprise centrifuging, e.g. 8000 g, the MTAB-TA GNR solution to separate the MTAB-TA GNRs from residual tannic acid and supernatant. Sterile water may be added to the MTAB-TA GNR solution and the solution may then be centrifuged to remove residual tannic acid from the MTAB-TA GNRs.

The functionalizing step may further comprise adding a solution of sodium chloride to the solution of tannic acid with MTAB-GNRs; adding a MOPS buffer (3-(N-morpholino) propanesulfonic acid) to the solution of tannic acid with MTAB-GNRs; and centrifuging the MTAB-TA GNR solution to separate the MTAB-TA GNRs from residual tannic acid and supernatant. As above, the functionalizing step may further comprise vortexing the tannic acid MTAB-GNR solution after each addition. Vortexing the solution may suspend the various components of the solution effectively, which may promote the formation of greater numbers of MTAB-TA GNRs.

The functionalizing step may further comprise adding sterile water to the MTAB-TA GNR solution and centrifuging to remove residual tannic acid from the MTAB-TA GNRs. The addition of sterile water and centrifuging may be repeated as necessary in order to remove residual tannic acid. This process is advantageous in that it results in the synthesis of MTAB-TA GNRs which are free of residual TA and supernatant, rendering the MTAB-TA GNRs ready for cellular uptake and imaging.

Tannic acid-coated 11-mercaptoundecyl trimethylammonium bromide (MTAB-TA) gold nanorods (GNRs) (MTAB-TA GNRs) exhibit no significant decrease in either in vitro cell viability or stress activation after exposures to A549 human alveolar epithelial cells. In addition, MTAB-TA GNRs demonstrate a substantial level of cellular uptake beyond that of known prior art GNRs, while displaying a unique intracellular clustering pattern. This clustering pattern significantly reduces intracellular aggregation, which preserves the GNRs NIR optical properties, and which is vital for biomedical imaging applications.

These results demonstrate how surface chemistry modifications may enhance and improve biocompatibility, may allow for higher rate of internalization with low intracellular aggregation of MTAB-TA GNRs, and may identify them as prime candidates for use in nanobased bio-imaging applications.

Materials and Methods
Cell Culture

The human lung, A549, cell line (ATCC) was maintained in RPMI 1640 cell culture media (ATCC) supplemented with 10% heat-inactivated fetal bovine serum and 1% penicillin-streptomycin. Cells were grown in a humidified incubator controlled at 37° C. and 5% $CO_2$. The same media composition was used for all GNR-exposure procedures.

Gold Nano Rods

CTAB, Silica, MTAB, TA, and GNRs were purchased from Nanopartz, Loveland, Colo., USA. CTAB-TA, and PEG GNRs were synthesized as previously reported. Both thiol PEGs (molecular weight 20,000 and 5000) were obtained from Nanocs (Boston, Mass.), and tannic acid (molecular weight 1701.2) was obtained from Sigma Aldrich (St Louis. Mo. USA).

GNR Characterization

The purity and spectral signature of the GNRs were analyzed before the experiment, using UV-Vis spectrometry on a Bio TEK Synergy HT™ (Winooski, Vt., USA) instrument. For evaluation of GNR size and morphology, nanoparticles (GNRs) in solution were placed onto a formvar carbon-coated copper TEM grid (Electron Microscopy Sciences) and dried. They were imaged with transmission electron microscopy (TEM) using a Hitachi H-7600 at an accelerating voltage of 120 kV. To assess the surface charge of the GNRs, zeta potential measurements were taken using laser Doppler electrophoresis on a Malvern Zetasizer™, Nano-ZS. Agglomerate sizes of the GNRs in media were determined through dynamic light scattering (DLS), also on a Malvern Zetasizer™ (Malvern Instruments, Mass, USA).

Cellular Viability Assessment

A549 cell viability was evaluated using the CellTiter 96® Aqueous One Solution (MTS) (Promega) which monitors mitochondrial function and MultiTox-Glo™ Assay (LCDC) (Promega) which sequentially measures two protease activities; one is a marker of cell viability, and the other is a marker of cytotoxicity. Cells were seeded into a 96-well plate at a concentration of $2 \times 10^3$ cells per well and the following day treated with the stated GNR conditions. After 24 h, the cells viability was determined in accordance with the manufacturer's protocol.

Measurement of ROS Generation

The intracellular generation of ROS (reactive oxygen species) after GNR exposure was evaluated using CM-H2DCFDA (Invitrogen) which is based on intracellular esterases and oxidation that yield a fluorescent product that is trapped inside the cell. Cells were seeded into a 96-well plate at a concentration of $2 \times 10^3$ cells per well and the following day treated with the stated GNR conditions. After 6 h, the intracellular ROS generation was determined in accordance with the manufacturer's protocol.

Quantification of Intracellular GNRs

A total of $1 \times 10^5$ cells/well were seeded on 12-mm diameter glass slides in a 24-well plate in triplicate then dosed with 5 µg/ml, GNRs for 24 h. The cell samples were then washed three times and treated with concentrated aqua regia for a minimum of 20 minutes to ensure full digestion of samples. The samples were then diluted to a final concentration of 3-1% HCl to $HNO_3$, respectively. The intracellular gold concentration was determined through inductively coupled plasma mass spectrometry (ICP-MS) on a Perkin-Elmer ICP-MS 300D instrument (Santa Clara, Calif, USA). ICP-MS was conducted in standard mode with 20 sweeps per reading, at one reading per replicate, and three replicates per sample with a dwell time of 100 ms. A calibration curve was obtained using blank and four gold standard solutions (0

(blank), 2, 50, 100, and 300 µg/L), and the addition of an internal standard (bismuth) was done to ensure that no interferences were occurring.

CytoViva Darkfield Imaging

A549 cells were seeded at $1.25 \times 10^5$ cells per chamber on a 2-well chambered slide and grown for 24 h. The following day, the cells were given a dosage of 20 µg/mL GNRs for 24 h. After 24 h, the cells were fixed with 4% paraformaldehyde and incubated with Alexa Fluor® 555-phalloidin for actin staining and DAPI for nuclear staining (invitrogen). The slides were then sealed and imaged using a CytoViva 150 ultraresolution attachment on an Olympus® BX41 microscope (Aetos Technologies. Inc.).

Hyperspectral Imaging

A549 cells were seeded at $1.25 \times 10^5$ cells per chamber on a 2-well chambered slide and grown for 24 h and the following day were exposed to GNRs (20 µg/ml). After 24 h, the cells were fixed with 4% paraformaldehyde. The slides were then sealed and imaged using a CytoViva® hyperspectral imaging system (Auburn, AL., USA). Image capture times and settings remained constant for all samples. Finally, hyperspectral analysis was performed using CytoViva's hyperspectral image analysis software.

Cellular Internalization Studies

A549 cells were seeded in a 6-well plate at $6 \times 10^5$ cells/well for 24 h and then exposed to the stated GNRs (5 and 20 µg/mL) for the indicated duration, washed, and fixed overnight in 2% paraformaldehyde and 2% glutaraldehyde. The cells were then stained with 1% osmium tetroxide, washed, and subsequently dehydrated with ethanol dilutions ranging from 50 to 100%. The cells were then embedded in LR White resin and cured overnight at 60° C. under a vacuum, after which the samples were sectioned using a Leica® EM UC7 Ultramicrotome. Cell sections 70 nm in thickness were placed on a formvar carbon-coated copper TEM grid (Electron Microscopy Sciences) and were imaged. Transmission electron microscopy (TEM) was performed using a Hitachi® H-7600 with an accelerating voltage of 120 kV. Care was taken to ensure full evaluation of each sectioned sample for the well-represented images.

Statistical Analysis

All experimental results represent a minimum of three independent trials unless otherwise stated. Data are expressed as the mean±the standard error of the mean (SEM). Statistical calculations were performed using SAS™ (Version 9.1) or GraphPad™ Prism (version 5.02, GraphPad Software Inc. La Jolla, Calif, USA) to determine statistical significance at p values of <0.05, <0.01, or <0.001.

Results and Discussion

Gold Nanorod Characterization

Figure 1A:
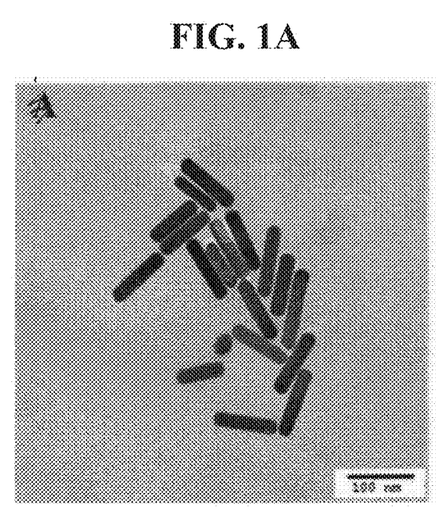
FIGS. 1A-1B depicts TEM images of gold nanorods (GNRs)
Figure 1B:
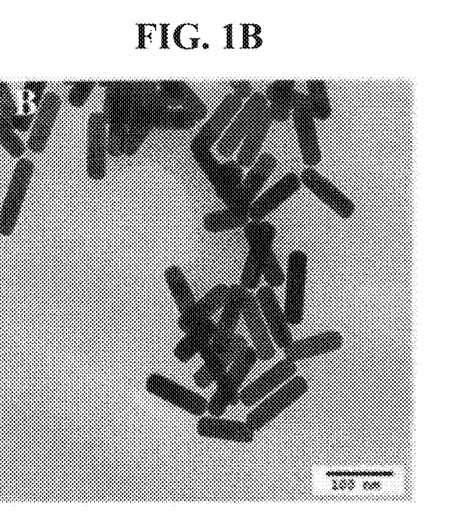
Figure 1C:
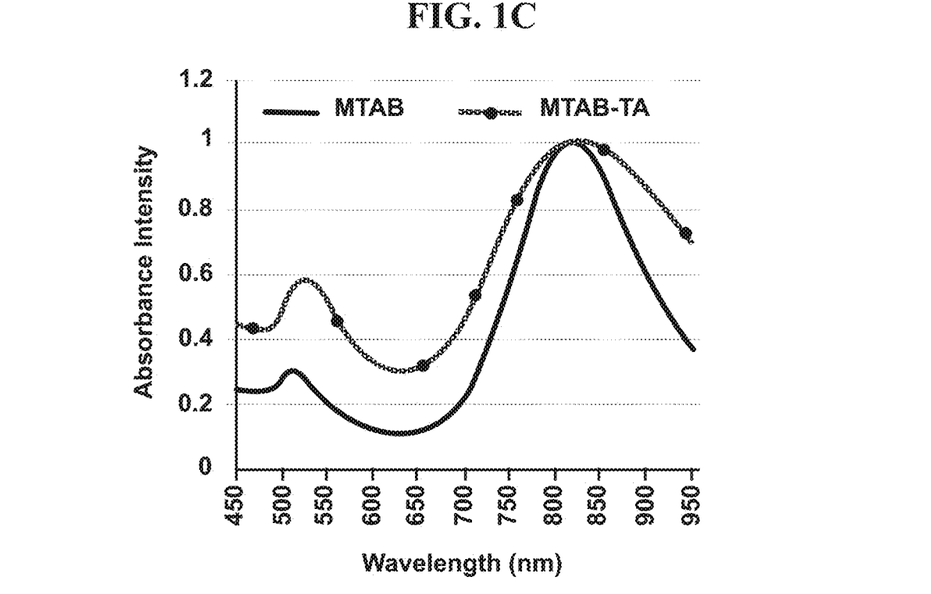
FIG. 1C illustrates the UV-Visible absorption spectra of MTAB and MTAB-TA GNRs.

GNR characterization was performed to determine their key physicochemical properties and to verify particle uniformity prior to experiments. TEM images demonstrated that GNR sets were uniform in size and morphology (FIGS. 1A-1C, Table 1). UV-Vis analysis confirmed predicted SPR peaks based on calculated AR (aspect ratio) (FIGS. 1A-1C). FIG. 1A depicts a representative TEM image of MTAB GNRs. FIG. 1B depicts a representative TEM image of MTAB-TA GNRs. FIG. 1C illustrates the UV-Visible absorption of both MTAB GNRs and MTAB-TA GNRs. As depicted in FIG. 1C, the absorbance intensity of the MTAB-TA GNRs is significantly higher than that of MTAB GNRs across the spectrum, except between 800-850 nm. To determine GNR surface charge, zeta potential analysis was performed on each particle (see Table 1 below). From this analysis, it was shown that MTAB GNRs were positively charged as expected due to MTABs quaternary ammonium cation. MTAB-TA GNRs displayed a negative surface charge, indicating that functionalization with TA was successful. When the GNRs were exposed to a protein-rich environment (culture media), both MTAB and MTAB-TA GNRs displayed a negative surface charge, −15.5 and −18.1 mV, respectively. Hydrodynamic sizes of GNRs in media showed that TA-coated GNRs were on average larger than MTAB GNRs.

TABLE I

Characterization of gold nanorods

| Name | Primary size (nm) | Aspect ratio | Surface chemistry | Surface charge (mV) | Hydrodynamic diameter in media (nm) |
|---|---|---|---|---|---|
| MTAB | 25 × 102 ± 4.0 | 4.1 | MTAB | 36.0 | 288.2 ± 4.0 |
| MTAB-TA | 25 × 104 ± 2.8 | 4.1 | MTAB-TA | −15.7 | 509.6 ± 66.9 |

Effects of GNRs on Cellular Viability and Stress

Figure 2A:
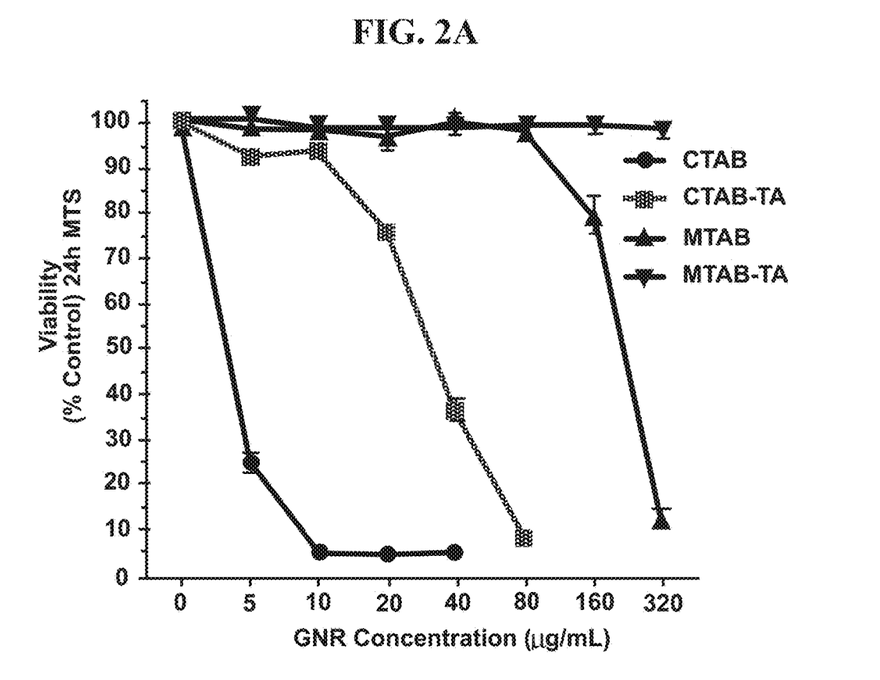
FIGS. 2A-2B illustrate a biocompatibility analysis of coated vs. uncoated GNRs.
Figure 2B:
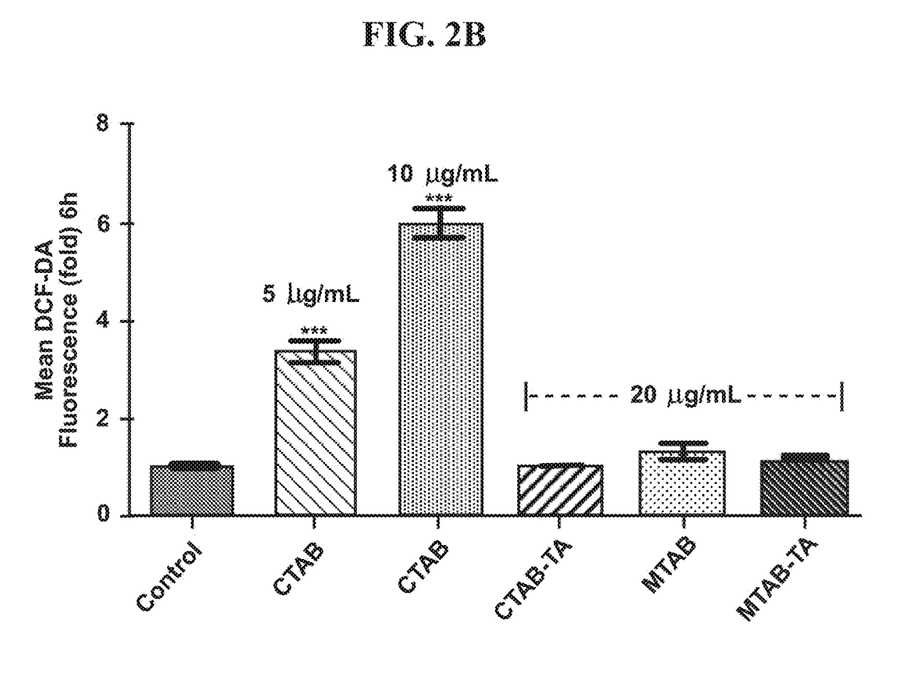

Since GNRs are known to exhibit toxicity linked to their physiochemical properties, multiple surface chemistries, charges, ARs, and concentrations of surface modifications on toxicity by evaluating membrane integrity and mitochondrial function were examiner. FIG. 2A illustrates an analysis of TA-coated versus uncoated CTAB GNRs and MTAB GNRs. Results indicate that the TA coating enhanced the biocompatibility of both CTAB GNRs and MTAB GNRs. and MTAB-TA GNRs exhibited no significant decrease in viability with concentrations as high as 320 µg/mL. FIG. 2B illustrates an ROS (reactive oxygen species) assay which demonstrated a significant increase in ROS after exposure to CTAB GNRs at concentrations as low as 5 µg/mL. After exposure to MTAB GNRs and MTAB-TA GNRs (20 µg/m). A549 cells showed no significant effects on their cellular viability with viability remaining over 95% after 24 and 48 h. The viability data demonstrate that the reported toxicity of CTAB-TA was not due to the TA overcoating, negative surface charge, or the AR of these GNRs, suggesting that the residual CTAB bilayer was the cause of the toxicity.

Next we examined cellular stress by measuring changes in reactive oxygen species (ROS) after cellular exposure to the various GNRs. The 6-h time point was chosen based on maximum ROS response before cell death. A549 cells showed no significant increase in ROS levels after exposure to MTAB GNRs and MTAB-TA GNRs, even at four times the treatment concentration of the CTAB GNRs that had significantly increased ROS levels (see FIG. 2B). Together, these results demonstrate the high biocompatibility of both MTAB GNRs and MTAB-TA GNRs. Statistical significance was determined using a one way ANOVA with Dunnett's post-hoc tests.

In view of their biocompatibility based on these initial findings and their longitudinal SPR peaks in the NIR "water window," we further explored the cellular association and in vitro hyperspectral signature of MTAB AR 4 GNRs with and without a TA coating.

Cellular Association and In Vitro Hyperspectral Signature

Figure 3A:
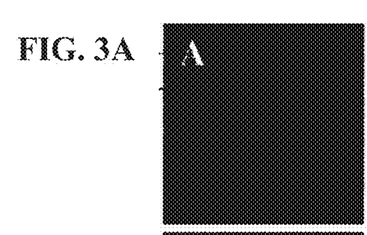
FIGS. 3A-3F depict representative darkfield and hyperspectral images with analysis of intracellular GNR optical properties.
Figure 3B:
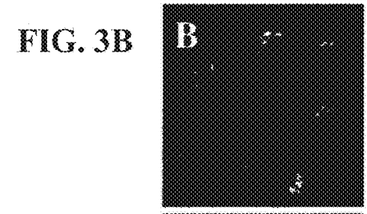
Figure 3C:
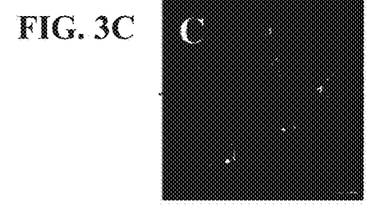

FIGS. 3A-3F illustrate representative darkfield and hyperspectral images with analysis of intercellular GNR optical properties. Visualization of cellular association of MTAB GNRs and MTAB-TA GNRs was illustrated using darkfield microscopy (see FIGS. 3A-3C). FIGS. 3A-3C illustrate fluorescent images following GNR exposure of 20 µg/mL, with FIG. 3A as the control sample. FIG. 3B is with MTAB GNRs. and FIG. 3C is with MTAB-TA GNRs. The fluorescent image results illustrate clustering of GNRs while the morphology of A549 cells was retained. A549 cells underwent actin and nuclear stainings with GNRs, which reflect white. Both GNRs interacted with A549 cells and had a high level of cellular association. MTAB GNRs and MTAB-TA GNRs appeared to be densely packed, suggesting that the associated and/or internalized GNRs are in clusters. In addition, the morphology of the A549 cells were retained, further confirming the biocompatibility of the GNRs.

Figure 3D:
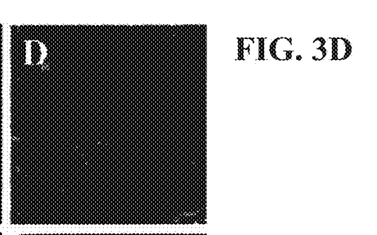
Figure 3E:
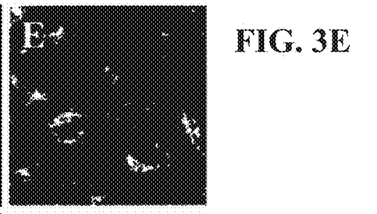
Figure 3F:
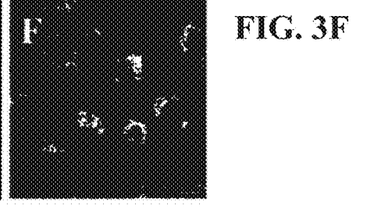

Next, we performed in vitro hyperspectral imaging (HSI) microscopy to investigate the GNR's optical properties after cellular association. HSI combines the use of darkfield microscopy and spectroscopy for the measurement of the reflectance spectrum at individual pixels in a micrograph. HSI analysis has been used successfully for characterizing gold nanoparticle aggregation, protein adsorption, and cell uptake in biological/cellular environments. This in vitro analysis of MTAB GNRs and MTAB-TA GNRs is critical, as many studies have shown that biological/cellular environments can alter the optical properties of GNRs and other nanomaterials. In this case. HSI analysis demonstrated that both GNRs had a strong association to A549 cells and appeared to indicate clustering of both MTAB GNRs and MTAB-TA GNRs (FIGS. 3D-3F). Hyperspectral images followed GNR exposure of 20 μg/mL, with FIG. 3D as the control sample. FIG. 3E is with MTAB GNRs, and FIG. 3F is with MTAB-TA GNRs. Results indicated that MTAB-TA GNRs presented a more desirable uniform clustering and spectral profile than MTAB GNRs based on their appearance in the hyperspectral images.

Figure 3G:
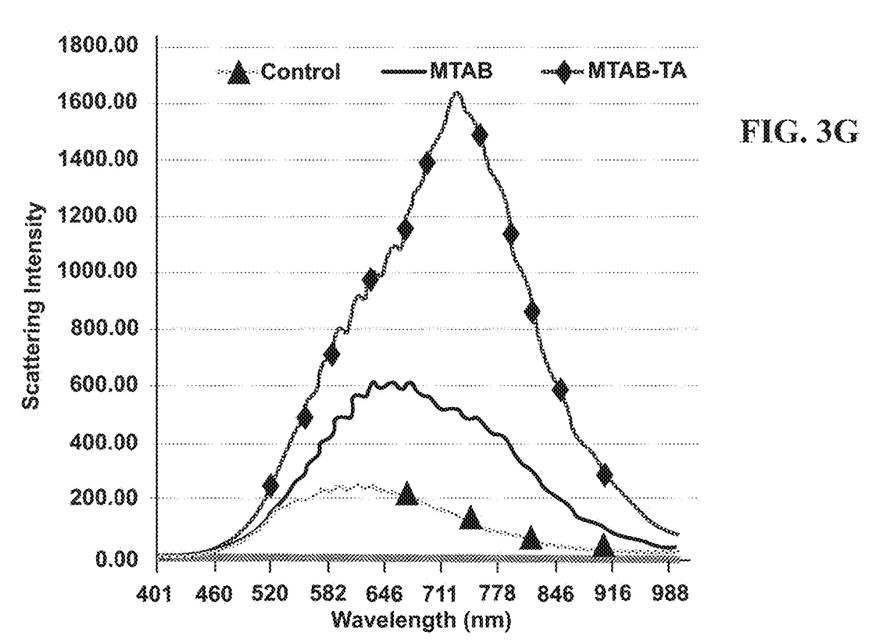
FIG. 3G illustrates an analysis of in vivo optical properties for GNRs.

In addition, the MTAB GNRs displayed a vast array of colors compared to the primarily white appearance of the MTAB GNRs, indicating a shift out of the NIR and into the visible spectra. Further, MTAB-TA GNRs have a more uniform clustering that allows for easier identification and delineation of the GNR clusters. Next, the reflectance spectrum of individual GNR clusters were measured and compiled to create a hyperspectral profile for both MTAB GNRs and MTAB-TA GNRs, as depicted in FIG. 3G. The hyperspectral analysis revealed that the spectral maxima were decreased in both hyperspectral profiles, compared to their spectral profiles as originally synthesized (see FIG. 1C). This blue shift in spectral maximas may have resulted from GNR intracellular aggregation with side-by-side assembly. This may have effectively lowered the GNRs' AR, resulting in the changes exhibited in the hyperspectral profile. The hyperspectral profile of MTAB-TA GNRs (n=385) revealed a sharper peak still within the NIR target "water window" ($\approx$732 nm). The shift seen with the MTAB-TA GNR clusters may be the result of protein corona formation and/or the orientation and proximity of the GNR to each other in the clusters after cellular association. In contrast, the hyperspectral profiles of MTAB GNRs (n=194) and control (n=335) displayed broad peaks that were located primarily outside the target NIR window ($\approx$630-679 and $\approx$550-634 nm, respectively).

In addition. MTAB-TA GNRs demonstrated a greater than 2.5-fold increase in scattering intensity over the MTAB GNRs after cellular association. Together, these results suggest that the MTAB-TA GNR form uniform GNR clusters that may be better able to preserve their NIR optical properties after cellular uptake. This finding may be significant for nanobased bio-imaging and therapeutic applications, because a strong spectra profile in the NIR "water window" alter exposure to biological/cellular environments is required for optimum efficacy in biomedical applications.

One possible explanation of the differences in hyperspectral signatures between MTAB GNRs and MTAB-TA GNRs may be due to differences in GNR uptake. Another possible explanation could be due to differences in aggregation states after cellular association and/or internalization. To test these possibilities, we set out to examine MTAB GNRs' and MTAB-TA GNRs' uptake by inductively coupled plasma mass spectrometry (ICP-MS) and intracellular aggregation states by TEM.

Quantification and Visualization of Cellular Uptake

Quantification of cellular uptake in the MTAB GNRs and MTAB-TA GNRs (5 μg/ml) was determined by ICP-MS. Both MTAB GNRs and MTAB-TA GNRs exhibit a high level (44 and 41% of treatment, respectively) of cellular uptake (FIGS. 4A-4D) compared to 1.5% with PEG GNRs or 15% with Silica-coated GNRs. In addition, this finding suggests that the TA overcoating's negative surface charge has minimal impact on cellular uptake of MTAB-TA GNRs. These findings appear to differ from other studies that report that GNRs with a positive surface charge have a greater cellular association and uptake than GNRs with a negative surface charge. It was originally proposed that the positive surface charge on the GNRs was attracted to the negatively charged membrane of the cell resulting in higher GNR cellular association. However, when GNRs of differing charges are placed in a biological environment (or simulated biological environment such as culture media), the GNRs will take in the charge of the biological environment. This is in agreement with our findings that both MTAB GNRs and MTAB-TA GNRs displayed negative surface charges of 15.5 and −18.1 mV, respectively. That TA has a strong attraction for protein and cellular membranes has been well documented. In addition, it has been reported that TA-coated gold nanomaterials have strong cellular association and unique form of cellular uptake. To test this hypothesis, we performed SDS-PAGE to evaluate the protein coronas of the GNRs in vitro conditions (10% FBS) and simulated in vivo conditions (100% FBS). We found that MTAB-TA GNRs had a high level of protein association with a similar protein profile compared to MTAB GNRs. We further quantified the relative amounts of albumin (bands at $\approx$66 kDa) present in the MTAB-TA GNRs' protein corona compared with the MTAB GNRs' protein corona. Results indicated that the MTAB-TA GNRs had a greater relative amount of albumin association under in vitro conditions (10% plasmon-resonance effect of FBS); however, under simulated in vivo conditions (100% FBS), MTAB GNRs had a greater relative amount of albumin association. Therefore, the MTAB-TA GNRs may form a distinctive protein corona that may account for their uptake properties. The finding that there is no significant difference in uptakes of the two GNRs further suggests that the differences seen between hyperspectral profiles is not significantly impacted by differences in cellular uptake of the two GNRs, Therefore, we next investigated the intracellular state of the GNRs, because previous studies have shown that the aggregation state of GNRs can affect their spectral profiles.

Figure 4A:
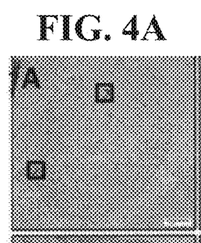
Figure 4A:
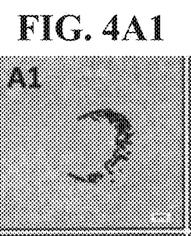
Figure 4A:
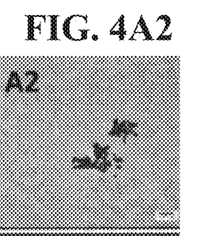
Figure 4B:
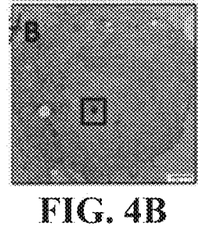
Figure 4B:
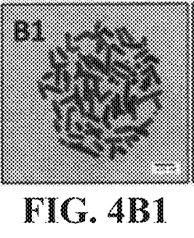
Figure 4C:
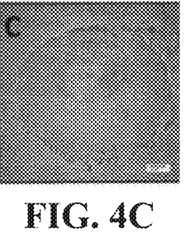
FIG. 4C depicts a TEM image of a control group in the GNR cellular uptake and analysis by ICP-MS.
Figure 4D:
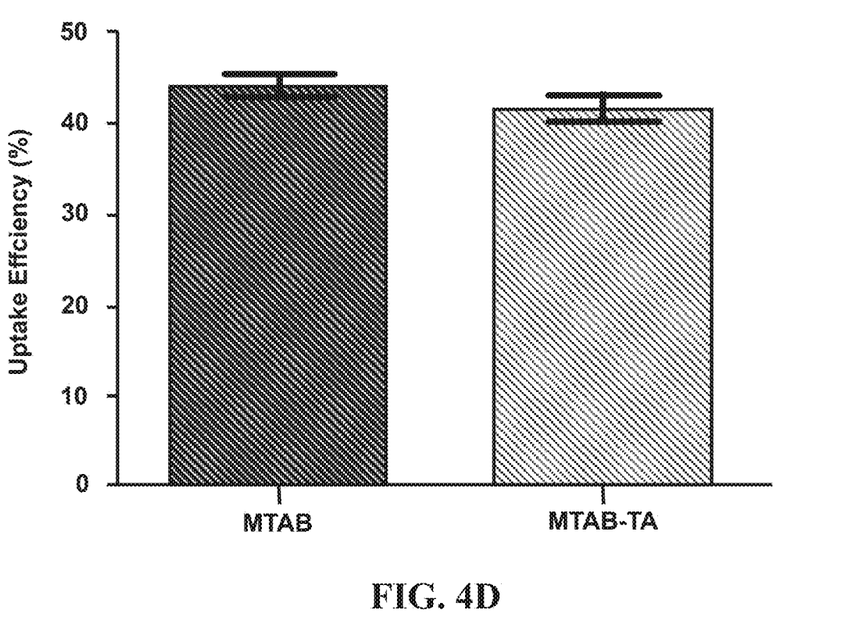
FIG. 4D graphically illustrates cellular uptake of GNRs by ICP-MS.

The distribution of MTAB GNRs and MTAB-TA GNRs AR4 (5 μg/ml) within the cell was observed using TEM (FIGS. 4A-4C). MTAB-TA GNRs demonstrated low aggregation of GNRs with a unique distribution pattern/cluster within the A549 cells. In contrast, MTAB GNRs appeared aggregated in dense clusters and/or tightly packed crest shape groupings. Representative TEM Images and GNR Uptake by ICP-MS after exposure to 5 μg/ml for 24 h for MTAB GNRs (FIG. 4A-4A2), MTAB-TA GNRs (FIG. 4B-4B1), and control sample (FIG. 4C). Results demonstrate intracellular aggregation of MTAB GNRs and low aggregation of MTAB-TA GNRs. FIG. 4D illustrates cellular uptake determined by ICP-MS. The ICP-MS results show high levels of uptakes of 44% for MTAB GNRs and 41% for MTAB-TA GNRs.

Visualization and Analysis of Intercellular Distribution Pattern

Figure 5A:
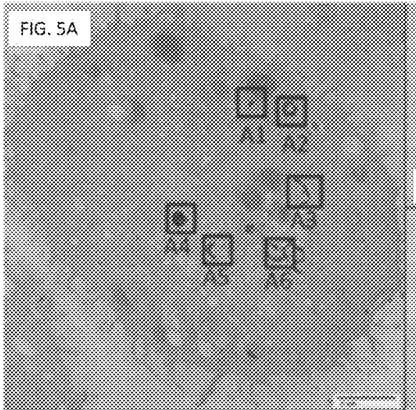
Figure 5A:
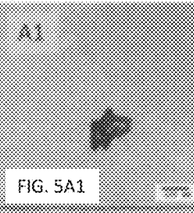
Figure 5A:
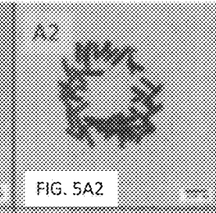
Figure 5A:
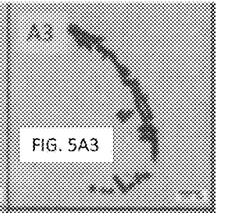
Figure 5A:
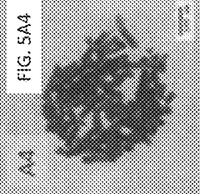
Figure 5A:
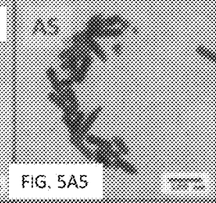
Figure 5A:
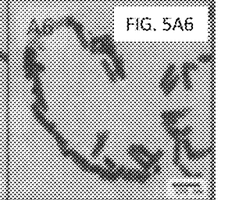
Figure 5B:
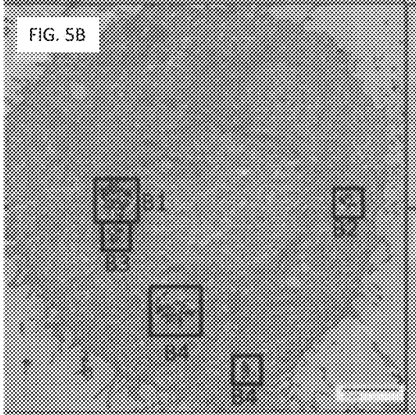
Figure 5B:
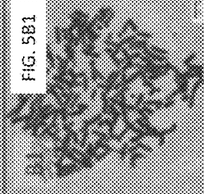
Figure 5B:
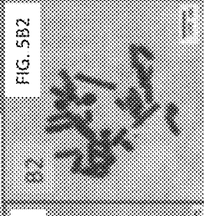
Figure 5B:
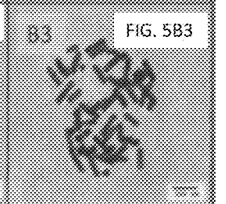
Figure 5B:
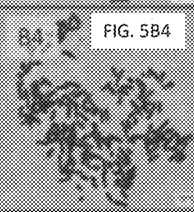
Figure 5B:
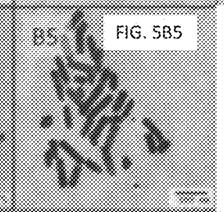

Since the concentration of nanoparticles, e.g. GNRs, can influence nanoparticle aggregation, cellular patterning was studied at 20 μg/ml. FIGS. 5A-5B5 present the intracellular distribution pattern of both MTAB GNRs and MTAB-TA GNRs by TEM analysis. The results demonstrate intracellular aggregation of MTAB GNRs (see FIGS. 5A-5A6) and low aggregation and unique distribution of MTAB-TA GNRs (see FIGS. 5B-5B5). At this new concentration, MTAB GNRs displayed small and large tightly packed clusters (FIGS. 5A1, 5A4), crest-shaped (FIGS. 5A3, 5A5, 5A6), and doughnut-shaped (FIG. 5A2) groupings with aggregation of GNRs. MTAB-TA GNRs again displayed distinctive GNR cluster patterns with low aggregation of GNRs (FIGS. 5B-5B5). Most GNRs are taken up through receptor-mediated endocytosis and further trafficked via an endo-lysosomal path. The MTAB GNRs appear to progress in the cells as follows: (1) First, small groupings of MTAB GNRs bind to the cell membrane: (2) Then the membrane invaginates with the attached MTAB GNRs and combines with similar groupings; (3) Next, GNRs can be seen as crest-shaped groupings; (4) GNRS are seen to be progressing to doughnut-shaped groupings; (5) Finally, they form as tightly packed clusters/groupings. In contrast, MTAB-TA GNRs do not display this pattern, possibly due to differences in their surface charge, protein corona, and/or a distinctive form of uptake. Regardless, it appears that the MTAB-TA GNR clusters are less compressed/densely packed than the MTAB GNR groupings.

Figure 6A:
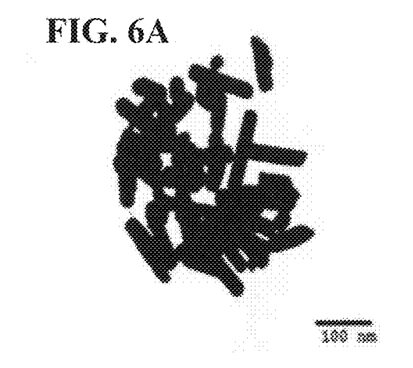
FIGS. 6A-6E depict an analysis of intracellular distribution of GNRs.
Figure 6B:
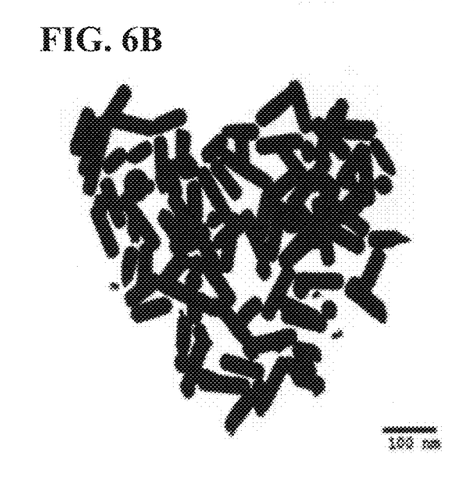
Figure 6C:
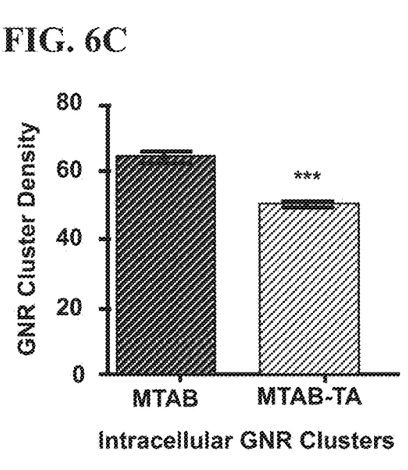
Figure 6D:
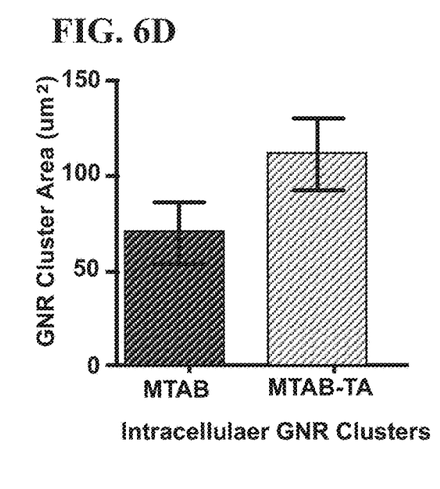
Figure 6E:
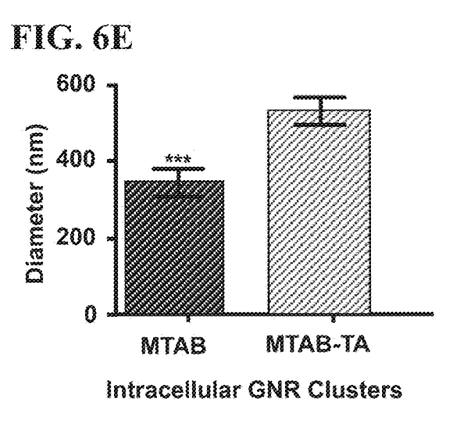

Next, we analyzed the GNRs clusters/groupings using ImageJ software (FIGS. 6A-6E). The MTAB GNR groupings (n=28) (FIG. 6A) were more densely packed than the MTAB-TA GNR groupings (n=24) (FIG. 6B) as reflected in the area fraction of GNRs over total area of clusters/groupings values of 64% versus 50%, respectively ($p<0.001$). FIG. 6C illustrates the average cluster density (area of GNRs/total cluster area) for both MTAB GNRs and MTAB-TA GNRs. FIG. 6D illustrates the average cluster area. FIG. 6E illustrates the average cluster diameter. The MTAB GNR groupings had a smaller average diameter (calculated as the mean of the smallest and the largest diameter measurements for each grouping) than the average diameter of MTAB-TA GNR cluster of 343 versus 534 nm, respectively ($p<0.001$). The total area of the MTAB-TA GNR clusters, as measured by ImageJ, appears to trend larger (see FIG. 6D); however, the difference was determined not to be statistically significant ($p=0.099$). Taken together, these results indicate that the differences in the intracellular distribution pattern may account for the preserved NIR spectral profiles of the MTAB-TA GNR clusters. Further, we examined the average diameter of extracellular GNR clusters in the TEM image using ImageJ. Results indicated that the diameter of extracellular MTAB-TA GNR clusters was larger than MTAB GNR clusters, namely, 310 versus 165 nm, respectively.

CONCLUSIONS

Figure 7:
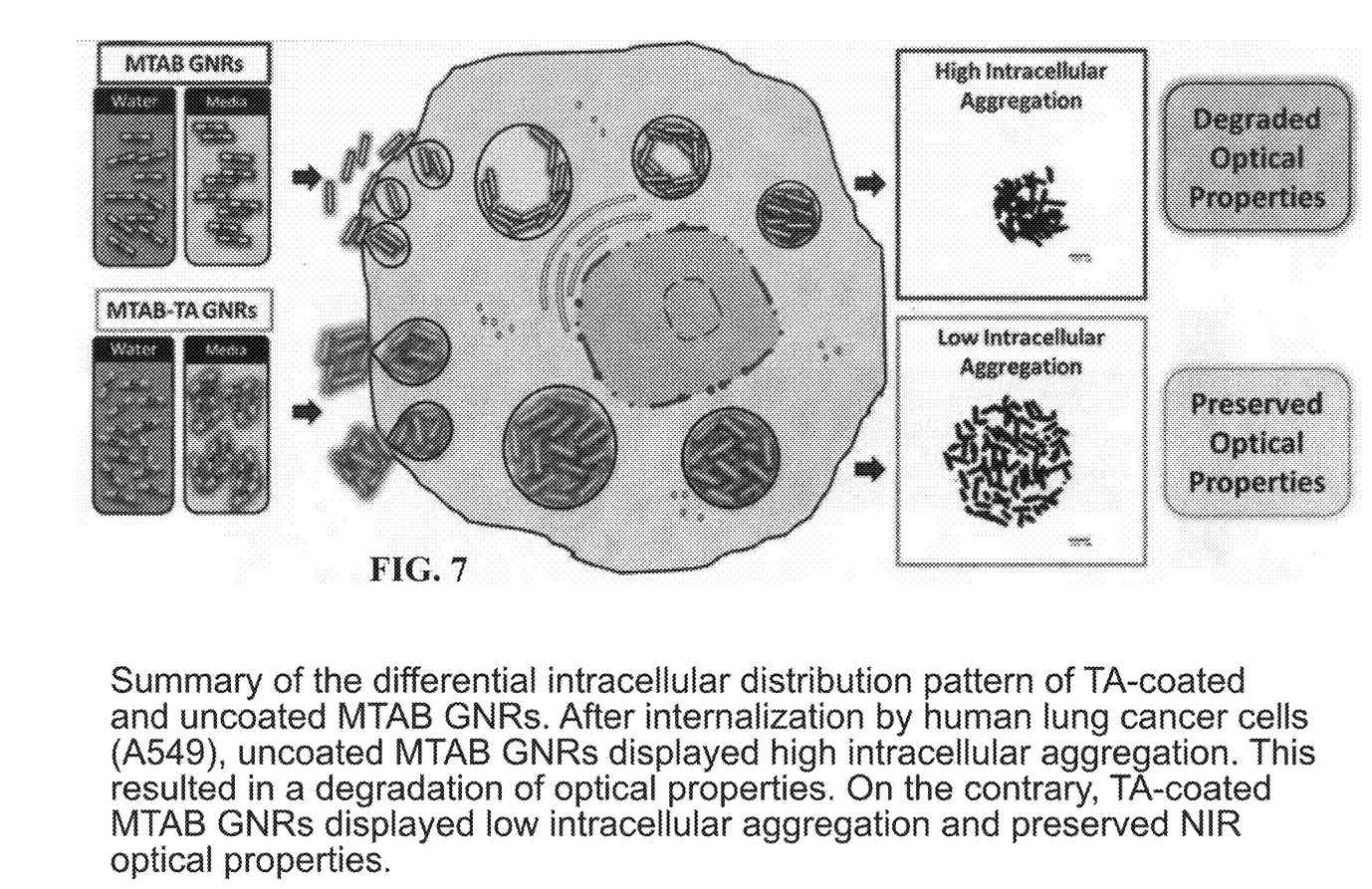
FIG. 7 illustrates a summary of the differential intracellular distribution pattern of uncoated and TA-coated MTAB GNRs.

When designing a gold nanorod for nanobased bioimaging applications, three problems are often difficult to overcome: (1) toxicity, (2) poor cellular uptake, and (3) loss of NIR optical properties due to particle aggregation in biological environments. In this invention, the GNR surface chemistry was modified by replacing CTAB with MTAB and overcoating with TA. This created a novel GNR (MTAB-TA GNR) that forms unique clusters, and exhibits no decrease in cellular viability, no indication of cellular stress, and no alteration of cell morphology, confirming its enhanced biocompatibility, as illustrated in FIG. 7. Further, in the A549 lung cancer cell line, MTAB-TA GNRs demonstrate a cellular uptake rate 27 times greater than the commonly used PEG GNRs, and 2.5 times greater than silica-coated GNRs. This high uptake rate enables a lower effective diagnostic and therapeutic working concentration. Finally, MTAB-TA GNRs display unique intracellular distribution patterns that not only preserve their NIR optical properties within the water window but also improve their spectral intensity greater than 2.5 times that of uncoated GNRs. This invention allows for the use of minimally invasive lasers, higher resolution imaging and more effective therapies.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. An 11-mercaptoundecyl trimethylammonium bromide gold nanorod (MTAB-GNR) coated with tannic acid (TA).

2. A method of synthesizing tannic acid-coated 11-mercaptoundecyl trimethylammonium bromide gold nanorods (MTAB-TA GNRs), the method comprising:
   presenting one or more 11-mercaptoundecyl trimethylammonium bromide gold nanorods (MTAB-GNRs) in solution; and
   functionalizing the MTAB-GNRs with tannic acid (TA) added to the MTAB-GNRs in solution, wherein the tannic acid is configured to form a coating around the MTAB-GNRs and MTAB-TA GNRs are formed.

3. The method of synthesizing tannic acid-coated 11-mercaptoundecyl trimethylammonium bromide gold nanorods (MTAB-TA GNRs) of claim 2, wherein the functionalizing step further comprises:
   vortexing the tannic acid MTAB-GNR solution.

4. The method of synthesizing tannic acid-coated 11-mercaptoundecyl trimethylammoniurn bromide gold nanorods (MTAB-TA GNRs) of claim 2, wherein the functionalizing step further comprises:
   adding a solution of sodium chloride to the solution of tannic acid with MTAB-GNRs.

5. The method of synthesizing tannic acid-coated 11-mercaptoundecyl trimethylammonium bromide gold nanorods (MTAB-TA GNRs) of claim 4, wherein the functionalizing step further comprises:
   vortexing the tannic acid MTAB-GNR solution.

6. The method of synthesizing tannic acid-coated 11-mercaptoundecyl trimethylammonium bromide gold nanorods (MTAB-TA GNRs) of claim 4, wherein the functionalizing step further comprises:
   adding a MOPS buffer (3-(A-morpholino)propanesulfonic acid) to the solution of tannic acid with MTAB-GNRs.

7. The method of synthesizing tannic acid-coated 11-mercaptoundecyl trimethylammonium bromide gold nanorods (MTAB-TA GNRs) of claim 6, wherein the functionalizing step further comprises:
   vortexing the tannic acid MTAB-GNR solution.

8. The method of synthesizing tannic acid-coated 11-mercaptoundecyl trimethylammonium bromide gold nanorods (MTAB-TA GNRs) of claim 6, wherein the functionalizing step further comprises:
   centrifuging the MTAB-TA GNR solution to separate the MTAB-TA GNRs from residual tannic acid and supernatant.

9. The method of synthesizing tannic acid-coated 11-mercaptoundecyl trimethylammonium bromide gold nanorods (MTAB-TA GNRs) of claim 8, wherein the functionalizing step further comprises:
   adding sterile water to the MTAB-TA GNR solution and centrifuging to remove residual tannic acid from the MTAB-TA GNRs.

10. The method of synthesizing tannic acid-coated 11-mercaptoundecyl trimethylammonium bromide gold nanorods (MTAB-TA GNRs) of claim 2, wherein the functionalizing step further comprises:
   adding a solution of sodium chloride to the solution of tannic acid with MTAB-GNRs; adding a MOPS buffer (3-(A-morpholino)propanesulfonic acid) to the solution of tannic acid with MTAB-GNRs; and
   centrifuging the MTAB-TA GNR solution to separate the MTAB-TA GNRs from residual tannic acid and supernatant.

11. The method of synthesizing tannic acid-coated 11-mercaptoundecyl trimethylammoniurn bromide gold nanorods (MTAB-TA GNRs) of claim 10, wherein the functionalizing step further comprises:
   vortexing the tannic acid MTAB-GNR solution after each addition.

12. The method of synthesizing tannic acid-coated 11-mercaptoundecyl trimethylammonium bromide gold nanorods (MTAB-TA GNRs) of claim 10, wherein the functionalizing step further comprises:
   adding sterile water to the MTAB-TA GNR solution and centrifuging to remove residual tannic acid from the MTAB-TA GNRs.

* * * * *